(12) United States Patent
Nelson et al.

(10) Patent No.: US 6,499,344 B2
(45) Date of Patent: Dec. 31, 2002

(54) APPARATUS AND METHOD TO OBTAIN REPRESENTATIVE SAMPLES OF OIL WELL PRODUCTION

(76) Inventors: Donald C. Nelson, 4408 Onyx Ct., Bakersfield, CA (US) 93308; Donald Wallace Ekdahl, 3031 21st St., Bakersfield, CA (US) 93301

( * ) Notice: Subject to any disclaimer, the term of this patent is extended or adjusted under 35 U.S.C. 154(b) by 0 days.

(21) Appl. No.: 09/829,407

(22) Filed: Apr. 9, 2001

(65) Prior Publication Data

US 2002/0020215 A1 Feb. 21, 2002

Related U.S. Application Data

(63) Continuation-in-part of application No. 09/340,517, filed on Jun. 28, 1999, now Pat. No. 6,212,948.

(51) Int. Cl.$^7$ .................. G01N 25/18; E21B 49/08; G01F 13/00
(52) U.S. Cl. ................. 73/152.23; 73/152.18; 73/152.31; 73/152.42; 73/61.41; 73/64.44; 73/64.56; 166/250.16; 166/264
(58) Field of Search .................. 73/152.42, 152.23, 73/152.18, 152.31, 61.41, 64.44, 64.56, 152.52, 152.29, 53.04, 64.55, 19.05, 861.04; 166/250.16, 250.15, 264, 250.01

(56) References Cited

U.S. PATENT DOCUMENTS

| | | | |
|---|---|---|---|
| 3,130,808 A | 4/1964 | Walker, Jr. | 181/50 |
| 3,660,644 A | 5/1972 | Hammond et al. | 235/95 PL |
| 4,015,194 A | 3/1977 | Epling | 324/1 |
| 4,813,270 A | 3/1989 | Baillie | 73/61 R |
| 4,901,563 A | 2/1990 | Pearson | 73/151 |
| 5,209,765 A | 5/1993 | Kolpak et al. | 55/168 |
| 5,211,842 A | 5/1993 | Tuss et al. | 210/87 |
| 5,283,001 A | 2/1994 | Gregoli et al. | 252/314 |
| 5,612,494 A | 3/1997 | Alexander | 73/152.55 |
| 5,633,470 A | 5/1997 | Song | 73/861.04 |
| 5,654,502 A | 8/1997 | Dutton | 73/152.18 |
| 5,865,247 A | 2/1999 | Patterson et al. | 166/252.1 |

Primary Examiner—Hezron Williams
Assistant Examiner—David J. Wiggins
(74) Attorney, Agent, or Firm—Donald D. Mon

(57) ABSTRACT

A well tester adapted to select among members of an oil well family to provide a purged and clean vessel to receive samples of well production that include gas and oil, and by selective use of production pressure and lease water under pressure, allow for the separation and separate measure of the oil and gas, and optionally to provide for improved sampling of production fluids with high gas/oil ratios.

11 Claims, 6 Drawing Sheets

APPARATUS AND METHOD TO OBTAIN REPRESENTATIVE SAMPLES OF OIL WELL PRODUCTION

CROSS REFERENCE TO RELATED APPLICATION

This is a continuation in part of applicants' copending U.S. patent application Ser. No. 09/340,517 filed Jun. 28, 1999, which patent application was issued as U.S. Pat. No. 6,212,948 on date of Apr. 10, 2001.

FIELD OF THE INVENTION

Apparatus and method for obtaining representative samples of the fluids produced by an oil well, and measuring the amounts of oil, water and gas in the sample.

BACKGROUND OF THE INVENTION

The need for accurate and timely oil well production data is critical. The extremely erosive and harsh environments in which well pumping systems operate create constant deterioration of the equipment, often resulting in rapid failure. To maintain production rates in the face of this situation, well operators invest substantial resources in well maintenance. For wells using steam drives and waterfloods, well servicing is frequently the highest non-energy cost.

Knowledge of the production performance of an individual well on a current basis is the most important tool for maximizing production from the well and optimizing reservoir management. Because of the well-known advantages of prompt, accurate and low-cost performance data, numerous testing systems have been devised. Despite extensive previous efforts, there still remain many unsolved disadvantages, resulting in uncertainly of accuracy of the data, and long testing periods because the sampling procedures were very slow themselves.

Early pioneers in production of oil from wells as early as about 1900 began to measure the performance of their individual wells. The early efforts were little more than collecting well production for a day or so, and measuring the gross output and the relative amounts of water and oil with a dip stick or tape measure. That method is still widely used, but is not truly sufficient when optimum and most economical production is the objective.

Open tank systems can indeed accurately measure the output of low production rate wells, but they take a very long time to collect the sample. Worse, production conditions can vary widely during that long period. A true production sample representative of a short preselected period of time can not be obtained with this practice.

Beginning in the 1960's this procedure was improved by providing tall, vertical, closed separators and using various mechanical devices to measure the levels and read them out. These largely succeeded because of the advent of pollution control rules, which adversely affected the earlier open tank samplers rather than because of any inherent sampling superiority. The closed samplers simply produced less pollution.

Beginning in the 1980's improved sensing devices became available, and their use improved the accuracy of the procedures but still their collection times were slow, and they did not provide for suitable purging between tests, leading to contaminated samples. Also the potential for measurement errors in low flow rate wells was and is much higher than it should be. Additional problems reside in the complexity and inaccuracies of the more modern sensors and measuring devices, especially at slow flow rates. Because of their sophistication, the initial costs and the costs of maintenance and operation of these newer systems are much higher than they should be.

Especially in periods of low oil prices at the well, it is essential not only to minimize operation and maintenance costs, but also to maximize production both of the well and of its field. Dollars are very scarce in times of low oil prices, and any reduction of costs is not only welcomed but may contribute to the decision to keep a well or field in operation rather than to shut it down.

It is an object of this invention to provide sampling apparatus and method that can obtain a sample which is suitably small to reflect fluid produced in a relatively short time, even from low production rate wells. A single sampler has the capability to service a substantial number of wells, often up to 60 wells, and to provide frequent samples from them. Importantly, the lines leading to it are fully purged of fluid remaining from previous tests as is the apparatus itself so that the sample is truly representative of well production at a very specific time.

This apparatus can be operated manually. In practice, programs to cause the sequential operation of the valves will be provided. Such programs form no necessary part of the invention, and can readily be devised by persons skilled in the controls art.

This apparatus can be automated to perform its method on a programmed basis without supervision, and can also be programmed to alert the owner to any departure of a well's performance from previous samplings, thereby alerting the operator to potential problems in a particular well.

It is an object of this invention to provide with minimal effort a clear and receptive tester for sequential tests for individual of a group of wells, and to provide a simplified arrangement to determine gas proportions.

In addition wells whose gas/oil ratio is very high involve special problems in measuring the gas of the product, which it is one object of this invention to overcome.

BRIEF SUMMARY OF THE INVENTION

Sampling apparatus according to this invention includes a vessel having a bottom wall, a top wall and a vertically extending sidewall which form a sample chamber.

A water inlet passes through the bottom wall. A test fluid exit port passes through the top wall. A test fluid line opens into the vessel at a mid-elevation. A test fluid inlet valve controls flow from a test fluid supply line to the test fluid line. A purge line opens into the vessel at a lower elevation.

A sample exit sensor senses flow from the sample exit port, and a purge control valve controls flow from the purge line.

A return line returns fluid from the vessel to a point of use. A flow line interconnects the purge line and the sample exit line at their intersection downstream from their respective valves. A selector valve is placed between said intersection and the fluid exit valve.

A gas discharge line is connected between said fluid exit line and said return line. A gas control valve and a gas flow meter are placed in the gas discharge line.

A flow meter device is placed in said return line.

A test fluid by-pass line interconnects the test fluid supply line to the return line. A by pass valve selectively controls flow through the test fluid inlet line and through the return line.

By suitable manipulation of the aforesaid valves along with the availability of lease water under pressure, test fluid under well pressure, and a suitable return to the system, a unique sampling process can be accomplished.

This system utilizes water from a separate water supply often called "lease water". This water is used and discarded as part of the procedure. This is not water from the samples.

A procedure according to this invention begins with the vessel full of water. First, the contents of the lines leading to the vessel wherever they may have come from will be forced into the vessel for a measured period of time. The pressure is that of the well production fluid. The water expelled by this incoming fluid passes through the flow meter. From this is calculated how long a time it will take for the flow from this well to completely form a suitable sample, or how large the sample will be in a selected period of time. This places produced material in the chamber.

The vessel next is closed and its contents permitted to settle (gas on top, water on the bottom, oil in between). During this time, test fluid from the well continues to purge the supply line through the by-pass.

Next gas is measured and purged. The lease water drives the fluids upwardly until liquid is sensed at a sensor (the supply line purge continuing). The gas flow through the gas flow meter measuring the gas content.

Oil is next purged from the vessel by further supply of lease water thereby driving oil out through the exit port. This driving action will continue until water has been sensed at the sensor for a given length of time, usually one minute. Thus, all of the piping downstream of the vessel will be purged.

Now a production sample is collected by opening the sample inlet valve and the water exit valve. The sample fluid will drive the purge water from the vessel and occupy the vessel by a known amount. After that time the vessel is closed and the sample water, gas and oil separate.

If desired for high oil/gas samples, a gas vent line is provided which relieves the vessel from excessive amounts of gas to enable a sufficient sample of oil to be obtained.

The above and other features of this invention will be fully understood from the following detailed description and the accompanying drawings, in which:

DETAILED DESCRIPTION OF THE INVENTION

Figure 1:
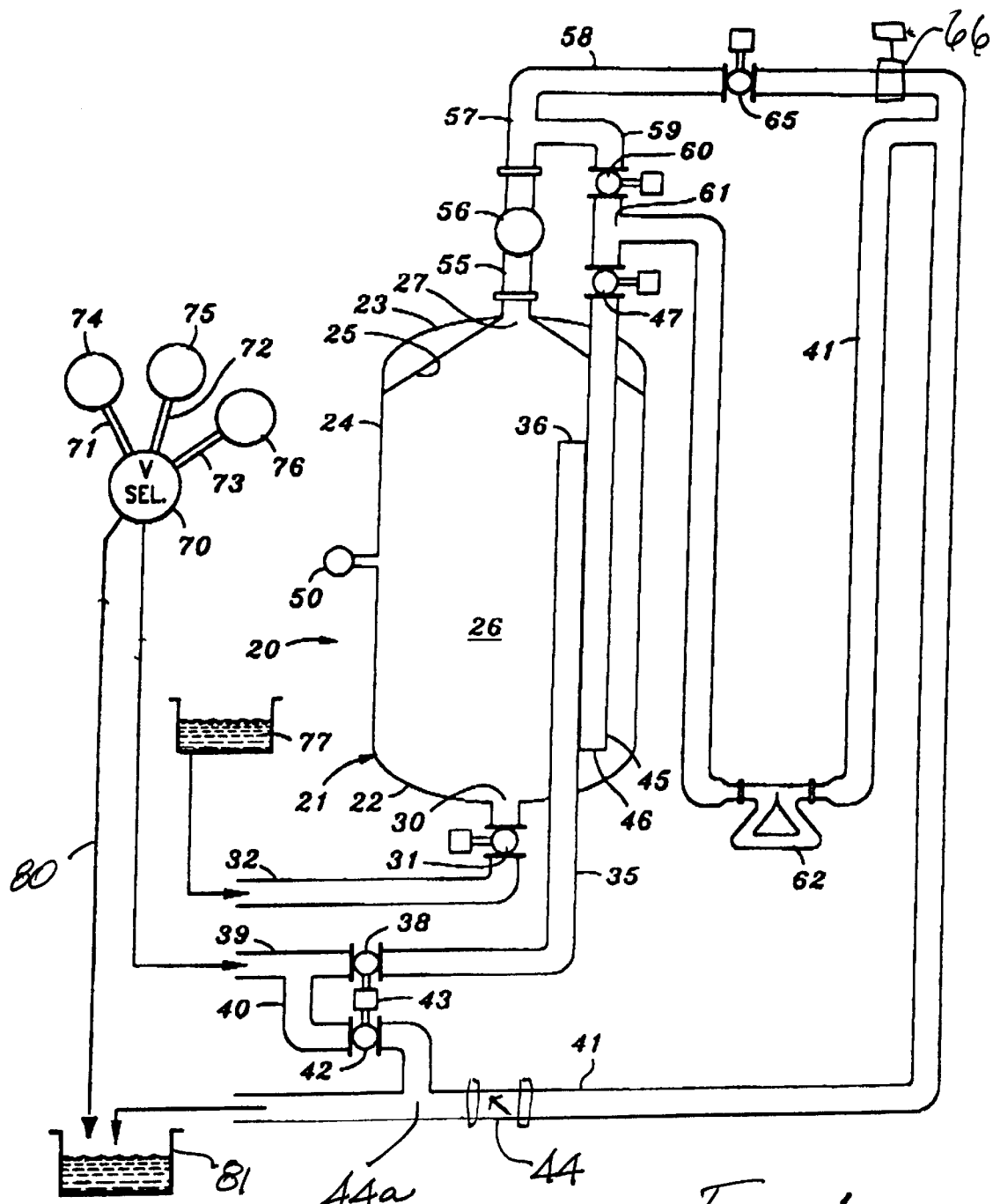
FIG. 1 shows the presently-preferred embodiment of a tester in its repose condition, coupled to a group of producing wells, shown principally in schematic notation.

A well tester 20 is shown in FIG. 1. It includes a vessel 21 which has a bottom wall 22, a top vessel wall 23 and a peripheral sidewall 24. It is a closed vessel with a substantial vertical dimension compared to its diameter. A frusto-conical chamber top wall 25 reduces the cross-section of sample chamber 26 at its top. It connects to an exit port 27 through the vessel top wall.

A water supply port 30 enters the sample chamber through the bottom wall. A water valve 31 is placed in a water line 32 which interconnects a supply 77 of lease water to the water supply port.

A test fluid line 35 enters the vessel, most conveniently through bottom 22. Its discharge end 36 is at a mid-elevation in the sample chamber. It could instead enter through the side wall, but the disclosed arrangement is much more convenient.

A test fluid inlet valve 38 interconnects the test fluid line 35 to sampling line 39. A by-pass line 40 interconnects a return line 41 and the sampling line 39. A by-pass valve 42 is disposed in the by-pass line. It will ordinarily be activated by an actuator 43 which sets valves 38 and 42 in alternate flow conditions.

A unidirectional check valve 44 is plumbed into return line 41 just upstream from the junction 44a of the by-pass line 40 and return line 41. The permissible flow through valve 44 is only from return line 41.

A purge line 45 extends from an inlet opening 46 near the bottom of the chamber, out of the chamber, conveniently through the top wall. A purge valve 47 is placed in purge line 45.

A pressure transducer 50 or other pressure measurement device senses the pressure inside the chamber.

An exit line 55 exists from the exit port 27. A liquid sensing probe 56 in the exit line will detect the interface or presence of a liquid, so it is sensitive to a gas/liquid interface or of a water/liquid interface when one passes the probe.

Exit line 55 branches at intersection 57 to a gas discharge line 58 and to a sample exit line 59. A selector valve 60 in line 59 is upstream of an intersection 61 of the sample exit line 59, return line 41, and purge line 45. A flow meter 62 measures the rate of flow of liquid through return line 41.

A gas vent valve 65 in gas vent line 58 controls flow through line 58 to return line 41. A gas flow meter 66 is fitted in gas vent line 58 downstream from gas vent valve 65.

As shown in FIG. 1, this tester is plumbed into a system which selectively provides flow from a selected well. A central station 70 is connected by collector lines 71, 72, 73 to individual wells 74, 75, 76. This valve will select the well, and through sampling line 39 will send product from a well being sampled to the tester. A family line 80 sends all production from wells not being sampled to a sump 81.

Lease water is supplied from a source 77. Return line 41 will return the output from the tester to sump 81 or to some other receptacle or system, along with production fluid from any other wells not in this family. To this sump are added the production through family line 80 from the wells in this family that are not being sampled at the time.

Later it will be appreciated that the sampled fluids and all production fluids from other wells are all returned to the sump along with what lease water is used in the testing. Lease water is used and disposed of the same as water in the sampled fluids. Sump 81 may also be regarded as a dehydration plant in which water is removed from product oil.

Controls for this system will customarily be programmed, but could instead be manually operated. The details of an automatic control are not an essential part of this invention and may readily be devised by a person skilled in the controls art. Care must be taken in the lines where flow and pressure and measured, to be certain that the velocities are such as to prevent stratification, and to permit collection of a sample in a suitably short time.

A unidirectional check valve 44 is plumbed into return line 41 upstream from junction 44a of the by-pass line 40 return line 41. The permitted flow through valve 44 is toward junction 44a.

Figure 6:
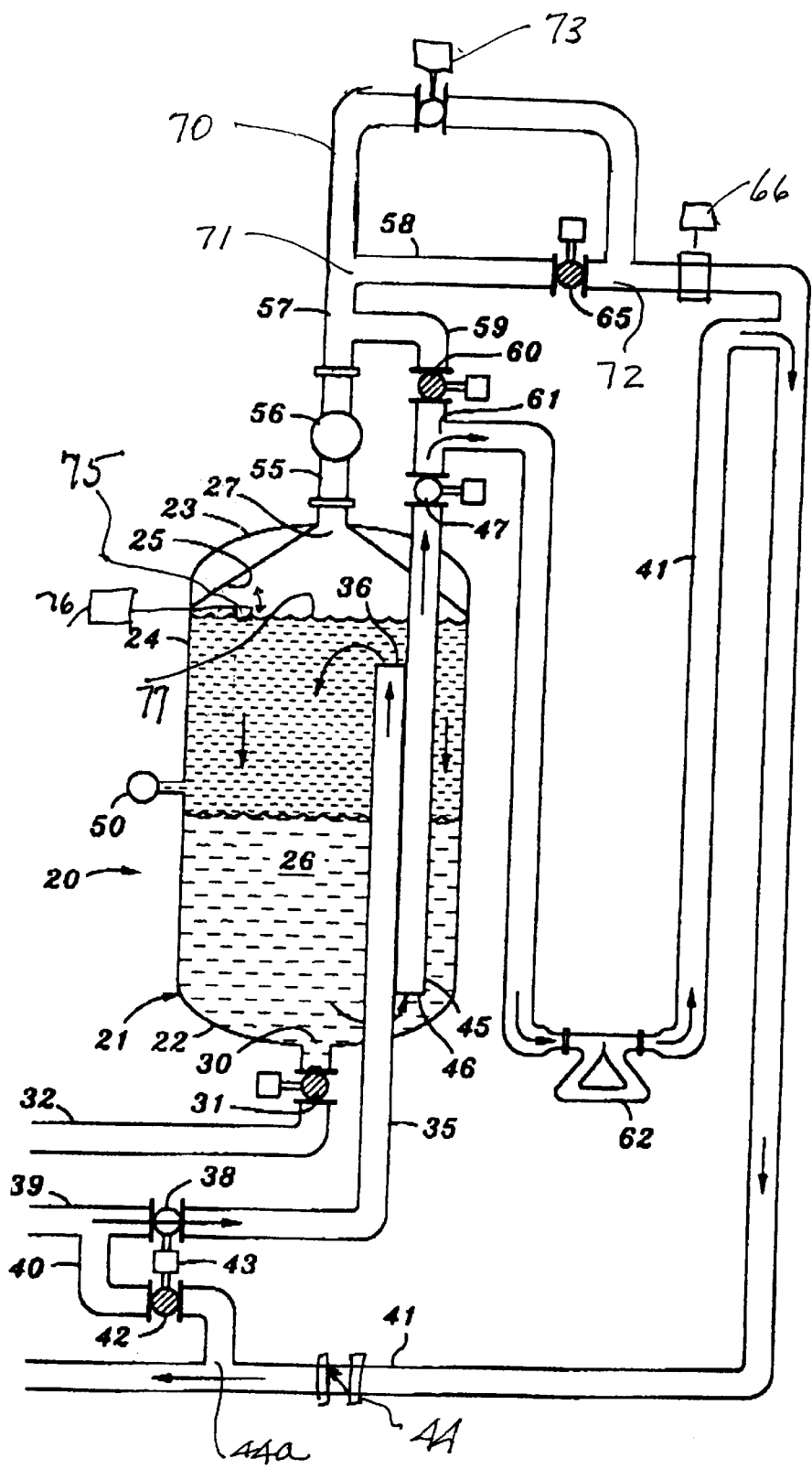
FIG. 6 shows a modified embodiment of the apparatus of FIG. 1. It provides for more precise analysis of the sample when the gas/oil ratio is very high. It utilizes the construction already described in FIG. 1, and bears the same corresponding numbers.

FIG. 1 illustrates the construction and operation of one embodiment of the invention. FIG. 6 shows a construction which is generally identical to FIG. 1, except that it includes modifications which make it even more useful for testing production of production from wells whose gas/oil ratio is quite high, for example, ratios as high as 600:1 and 1,600:1.

The following sequence of testing steps will be understood from the sequence of drawings in FIGS. 2–5, all relating to the configuration of FIG. 1.

Figure 2:
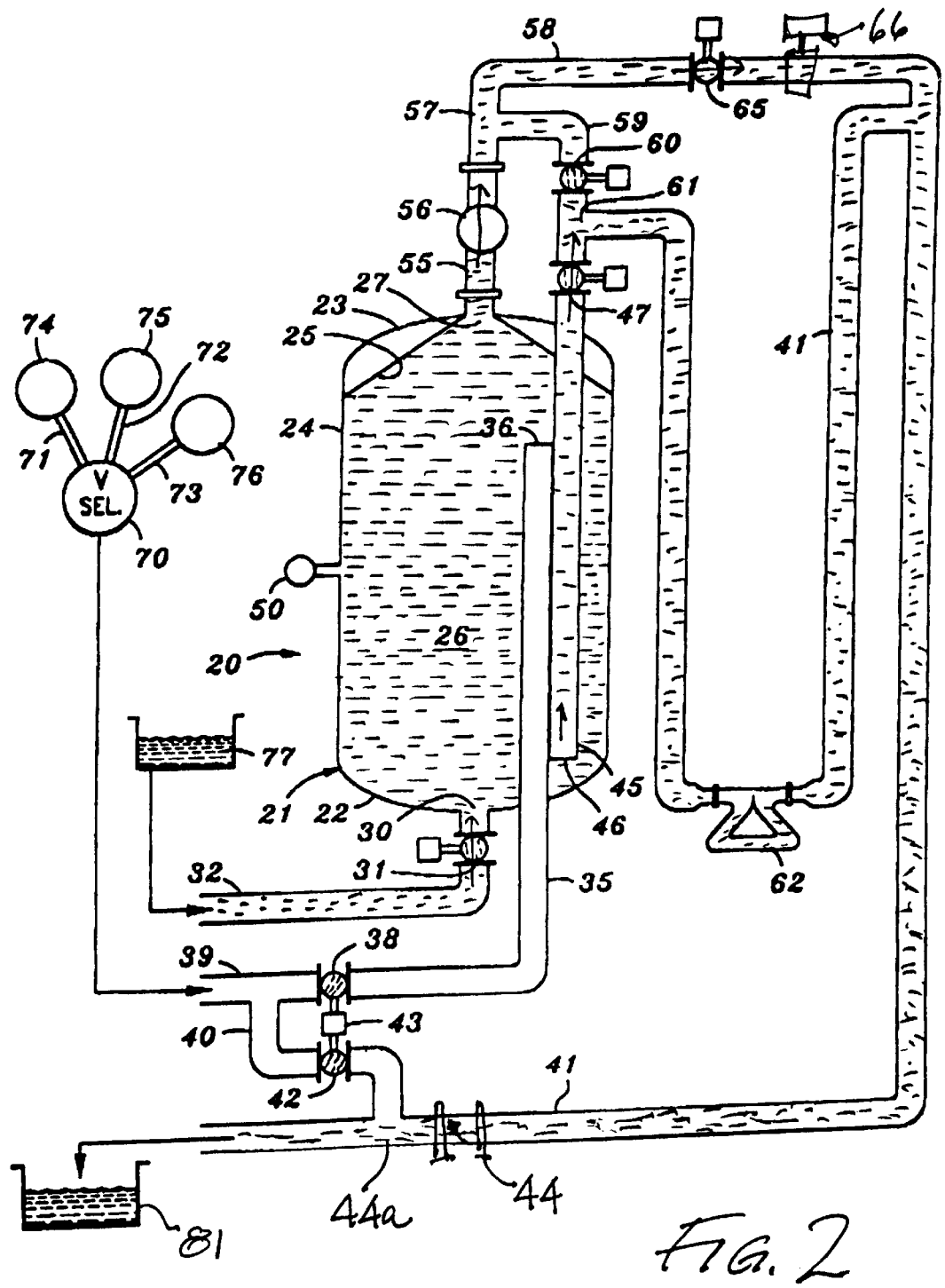
FIGS. 2–5 schematically show successive events in the process of this invention.

Vessel and Piping Purge Step (FIG. 2)

Assuming the tester is making a series of tests from a sequence of wells, this is the first step following the previous test or the startup of a fresh system. Its purpose is to assure that the system is cleared of substances from the previous test, and that the instrumentation will be free from fouling by residues from the previous test. It does this by introducing water into the system to displace such residues.

For this purpose water, shown in horizontal dashed lines, is introduced into the vessel through port 30 by opening valve 31.

It provides water at a selected flow velocity, preferably about 12 feet per second as measured across liquid sensing probe 56. Valve 60 is opened, valve 65 is closed, and valve 47 is closed. Flow is though flow meter 62. It washes the instrument clean of any oil which had not previously been removed.

After a preselected time, valve 60 will be closed and valve 47 opened to purge the purge line 45.

After another preselected period of time sufficient to clear purge line 45, purge valve 47 will close and gas vent valve 65 will be opened. This will purge gas vent line 58. These time periods are generally very short, so short that they may seem to be almost simultaneous. However, they are sequential steps.

This step leaves only the test fluid line not purged. However, because oil and gas will rise in water, its residual contents will have generally risen into the tank, to be displaced by water. The system will therefore have been entirely purged and is now filled with water.

Pre-test Sampling Line Purge Step

The sampling line 39 from selector valve 70 will contain production fluids from a previous test. Of course these are not to be passed through a vessel prepared for, or currently engaged in a successive test. Therefore, either before or after the procedure shown in FIG. 2, valve 38 will be closed and valve 43 opened by actuator 43. These settings are alternative, one of the valves being open and the other closed. Check valve 44 prevents back flow into the system.

Production fluids pass through the open by pass 40 until about 6 to 8 times the volume of sampling line 39 have flowed through the by-pass. This assures that the well sample to be tested will not be contaminated by fluids from the previously tested well.

Figure 3:
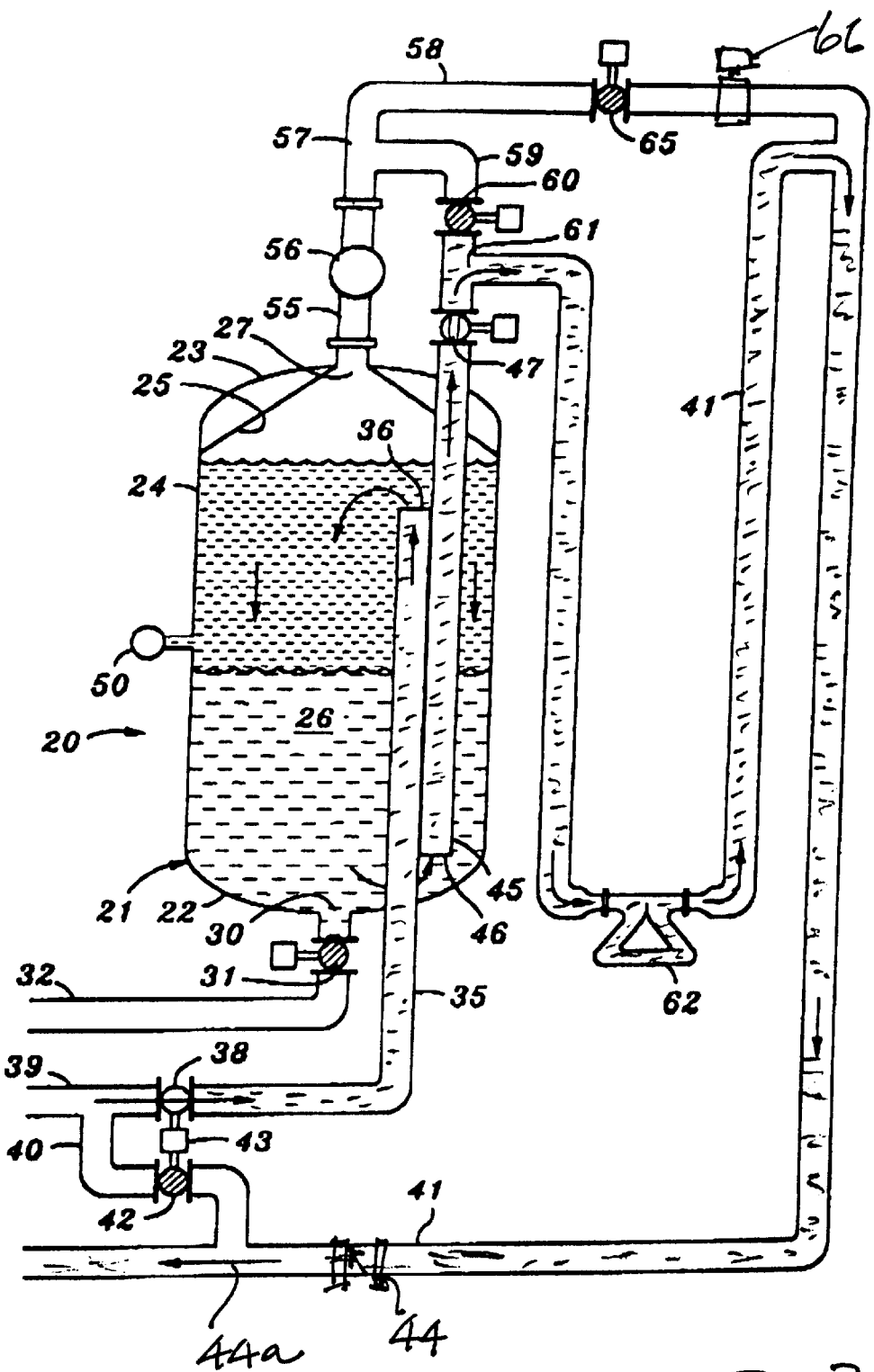

Gross Rate Measurement and Gas and Oil Collection Step (FIG. 3

Valves 31, 60 and 65 are closed. Valve 38 is opened to introduce produced fluids into vessel 26. Valve 47 is open. Now purge water from the previous steps flows through flow meter 62 (a Coriolis meter). This meter accurately measures the gross production rate from the well, even though it is measuring water flow rather than flow of other fluids. No produced fluids are displaced.

Also, a collection of oil and gas is being obtained in proportion to the gross flow rate input, which is known. This will continue until a predetermined (or preselected) percentage of the vessel volume has been displaced, at which time actuator 43 reverses the settings of valves 38 and 42, so that no more production fluids are sent to the vessel. Instead they will flow through by-pass line 40 to the sump. Therefore production from the selected well is never interrupted. Its production rejoins that of its family wells in the sump. Ultimately, so do the tested fluids. The tester is now ready for further measurement steps.

Settle Step

The condition reached in the foregoing step is allowed to persist. The sample is completely held in the system by the closed valves, while production fluids continue to flow through the by-pass. This settle step is intended to give the sample time to separate into its phases, water on the bottom, oil in the middle, and gas on top. In some slow-flowing wells, where the tester may be responding sequentially to wells having varying flow rates, the previous gross rate measurement and collection step may have to be repeated enough times to obtain an oil sample of suitable size. The gross production will, of course, have been measured for each repetition. In whatever event, the sample to be tested will now have settled into its phases, and measurements can proceed.

Figure 4:
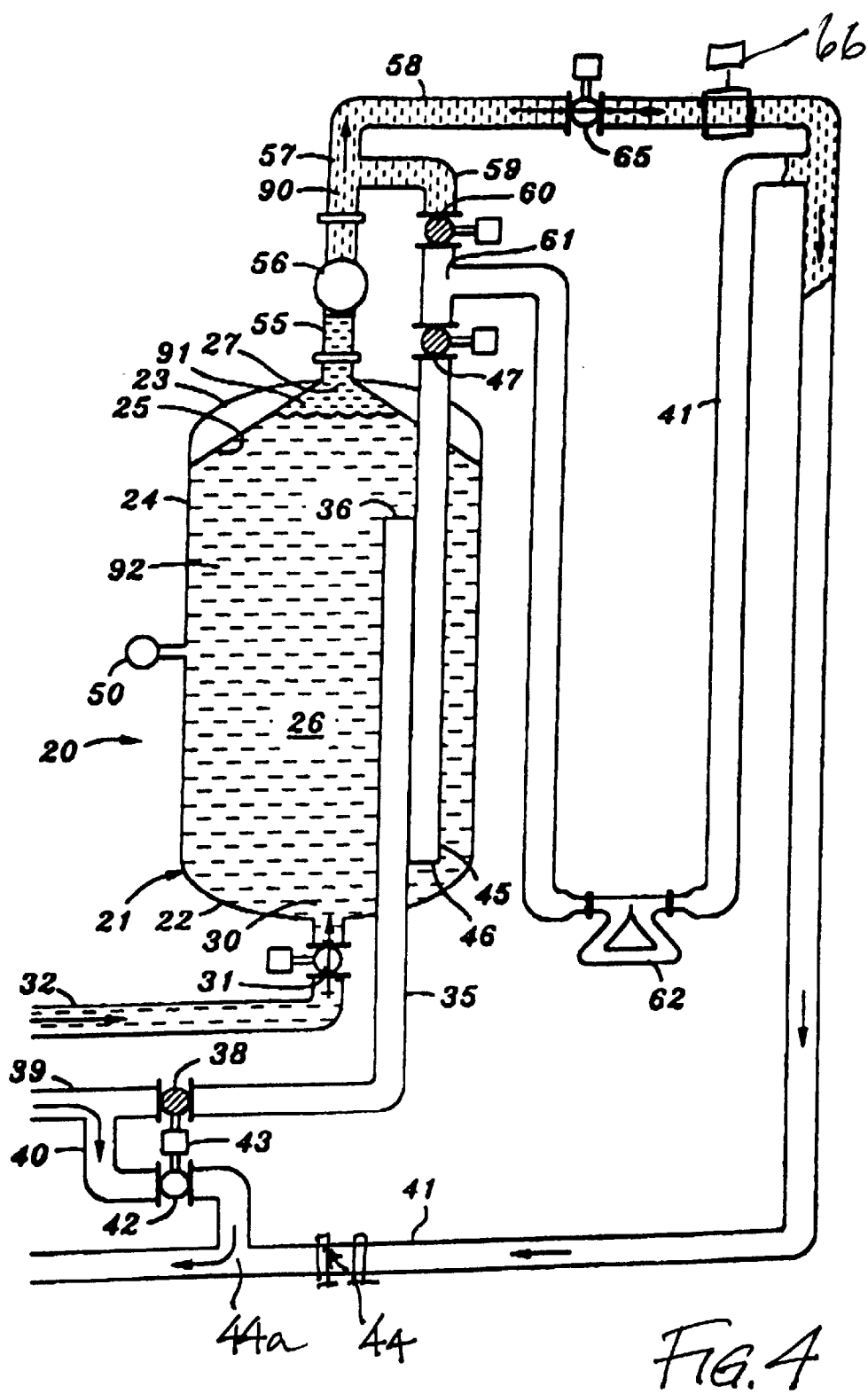

Gas Measure Step (FIG. 4)

There are two procedures available to measure the gas. The first procedure is preferred, but if the expense of a gas flow meter 66 cannot be justified, the second procedure is available, which does not need it.

In the first procedure shown in FIG. 4, lease water is supplied under pressure to the vessel by opening water supply valve 31. Gas vent valve 65 is opened, and the volume of gas is measured by gas flow meter 66. This will continue until probe 56 senses oil instead of gas because the interface between gas and oil has arrived at the probe. Then valve 65 is closed and valve 60 is opened. This will conclude the gas measure step.

The second mode for gas measurement, which does not require the use of gas flow meter 66 relies on the application of Henry's Law of compressibility. In this step, the vessel pressure is known at the start. Lease water is admitted into the vessel through valve 31 to raise the pressure by a known amount, perhaps 50 psi. Then valve 31 will be closed.

Valve 47 will now be opened releasing water through purge line 45 which flows through flow meter 62 to return the vessel to
its previous pressure, at which time valve 47 will close. Valve 60 was always closed. The volume of water measured by flow meter
62 is equated to gas volume, and thereby the gas content is measured.

Gas Purge Step

This step inherently follow the gas measurement step. The gas will have been purged from the vessel, and the flow of fluid will now be through valve 60, valve 65 being closed.

Figure 5:
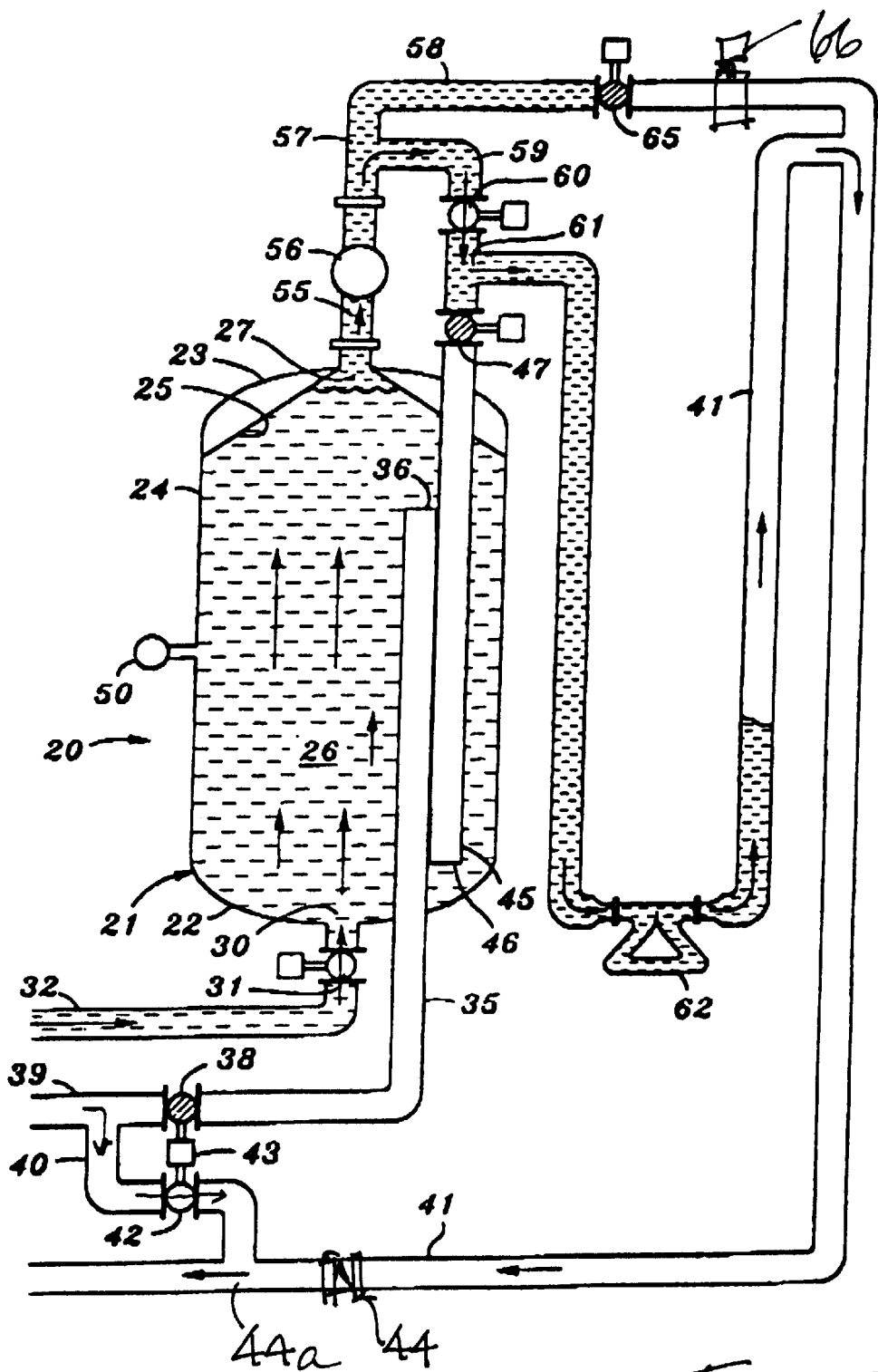

Oil Measure Step (FIG. 5)

Now the flow of fluid which is oil (the gas having been purged), passes through valve 60 and flow meter 62, impelled by lease water admitted to the vessel through valve 31. It continues until probe 56 senses water-the interface between oil and water. The volume which has passed the flow meter is known. To it is added the known volume of the lines ahead of it. The sum is the oil volume of the sample.

The reader will now recognize that he has been in this cycle before. The gas and oil of the sample have been measured, and all or most of the system is filled with water. Then the procedure is repeated, starting with step 1, except this time for a different one of the wells.

A comparison of FIGS. 1 and 6 shows in FIG. 6 the addition of a gas discharge line 70 from junction 71 between lines 57 and 58 to a junction 72 downstream from gas vent valve 65. Junction 72 is between gas vent valve 65 and gas flow meter 66. A gas discharge valve 73 is fitted in line 70. Gas discharge valve 73 is preferably a smaller valve than gas vent valve 65, perhaps a ½ inch valve compared to a 2 inch valve, to provide for lesser flow rates. A level sensor 75 is placed in the vessel, and is sensitive to the gas/liquid interface.

A sensor circuit 76 responds to the sensor. It will sense the presence or absence of a sufficient sample by responding to the gas/oil interface 77. A suitable example of a sensor is shown as a float mounted to a pivoted arm, whose position is responded to by the sensor circuit. Alternatively, a rod (not shown), electronically operated and sensitive or electronically responsive to the location of oil along its vertical length can be used, and its output utilized by the sensor circuit.

Some wells produce vastly larger quantities of gas than oil. Ratios of 1000:1 are common. In such situations, in order to collect a suitable and sufficient oil sample, very large volumes of gas must be passed and measured. These gas volumes emanate from the oil and rise to the top. When the vessel is filling, the gas vent valve will accommodate to the rapid flow of gas, which is measured by gas flow meter 66.

When the oil level finally reaches its desired level, as detected by the sensor, a lesser flow rate will often be preferred. In this event, gas vent valve 65 will be closed, and the smaller gas discharge valve 73 will be opened. Gas passing through either or both of these valves will be measured by flow meter 66. In whatever event, until a sufficient volume of oil is collected, the large volumes of gas will more speedily be removed so the oil can be collected more quickly.

This invention is not to be limited by the embodiments shown in the drawings and described in the description, which are given by way of example and not of limitation, but only in accordance with the scope of the appended claims.

What is claimed is:

1. A well tester for obtaining and assaying a production sample of test fluids from an oil well to learn its production rate, and content of gas if any, oil and water, said tester comprising:

a closed vessel having an internal chamber with a lease water supply port, an exit port, and a purge port;

a lease water supply line connected to said lease water inlet port and a lease water valve in said lease water line selectively to open or to close said lease water line to flow of fluid;

a test fluid line entering said chamber with a discharge end at a mid-elevation therein, a test fluid inlet valve in said test fluid line selectively to open or to close said test fluid line to flow of fluid;

a sampling line receiving test fluid from a source connected to said test fluid inlet valve;

a return line to return fluids;

a by-pass line interconnecting said test fluid line upstream from said test fluid inlet valve to said return line;

a by-pass valve in said by-pass line selectively to open or to close said by-pass line to flow of fluid;

a purge line through said vessel having an inlet end near the bottom of the vessel;

a purge valve in said purge line selectively to open or to close said purge line to flow of fluid;

a pressure sensor in said chamber to measure pressure therein;

an exit line connected to said exit port;

a liquid-sensing probe adapted to sense a gas/oil and an oil/water interface, disposed in said exit line;

a gas discharge line branching from said exit line;

a gas control valve in said gas discharge line selectively to open or to close said gas discharge line to flow of fluid;

a gas flow meter in said gas discharge line;

a sample exit line branching from said exit line;

a selector valve in said sample exit line selectively to open or to close to fluid flow;

said return line being joined to said sample exit line between said purge valve and said selector valve;

a flow meter to measure rate or volume of fluid flow in said return line;

said return line connecting to said gas discharge line downstream from said gas control valve;

whereby with selected settings of said valves, the tester and the supply lines leading to it may be substantially purged of prior samples, the rate of well production determined, the volume of sample obtained in a given time known, and the absolute and relative amounts of oil and water, and gas if present, may be learned.

2. Apparatus according to claim 1 in which a frusto-conical top wall in said chamber narrows to said exit port, said chamber having a substantial vertical dimension.

3. Apparatus according to claim 1 in which said test fluid line enters said chamber, extends upwardly into said chamber, and said purge line extends downwardly into said chamber, the outlet end of the test fluid line being at a higher elevation than the entry end of the purge line.

4. Apparatus according to claim 1 in which a gas discharge line by passes said gas vent valve, with a gas discharge valve therein, upstream from said gas flow meter.

5. A well tester according to claim 1 in which a unidirectional check valve is placed in said return line, upstream from its intersection with said by-pass line.

6. A well tester according to claim 1 in which a gas discharge line incorporates a gas discharge valve, said gas discharge line by-passing said gas vent valve from said gas vent line to said return line, upstream from said flow meter.

7. A well tester according to claim 6 in which a unidirectional check valve is placed in said return line, upstream from its intersection with said by-pass line.

8. Apparatus according to claim 1 in which a depth sensor is placed in said vessel to sense the location of a gas/oil interface, whereby to enable the gas/oil interface to be maintained at a selected level while gas is being discharged from the vessel.

9. A well tester according to claim 8, said sensor controlling said gas discharge valve, and said gas vent valve.

10. A process for obtaining and assaying a production sample from an oil well utilizing a well tester having a closed vessel forming an internal chamber with a lease water inlet line from a source of leased water under pressure entering said chamber; a test fluid line from a source of production fluid entering said chamber and discharging at a mid-elevation therein; a purge line exiting said chamber from a lower elevation therein; an exit port at the top of said chamber; a sensor in said exit line responsive to gas/oil and oil/water interfaces; a return line; a gas vent line branching from said exit line; said return line branching from said exit line; a flow valve in said return line; a lease water valve in said lease water supply line; a gas vent valve in said gas vent line; a gas flow meter in said gas vent line, a purge valve in said purge line; a selector valve in said exit line; said return line joining said exit line between said selection valve and said purge valve; a flow meter in said return line; a test fluid inlet valve in said test fluid line; a by-pass line between said test fluid inlet valve and said return line; and a by-pass valve in said by-pass line;

said process comprising the following steps in the order recited;

a. with the chamber full of water, opening the test fluid inlet valve, closing the by-pass valve, opening the purge valve and closing the selector valve and gas control valve, and forcing well fluid into-said chamber and through the flow meter for a measured period of time, thereby to learn the time required to purge lines leading to the chamber of well fluids from other wells;

b. then closing the test fluid inlet valve, opening the by-pass valve, closing the gas control valve and opening the purge valve, thereby permitting the contents of the chamber to settle, while well fluids flow through the by-pass line;

c. then opening the gas control valve, closing the purge valve, and opening the lease water valve, injecting lease water into the chamber to expel gas until the interface sensor senses the presence of an air/oil interface;

d. then opening the selector valve and closing the gas control valve, injecting lease water into the chamber until water is sensed by the sensor, and continuing for a period of time sufficient to purge the system of previous content, using lease water;

e. then closing the lease water valve by-pass valve and selector valve, and supplying well tester fluids to said chamber while measuring the rate or volume of lease water passing through the flow meter as a measure of well fluids injected into the chamber during a selected period of time;

f. then closing the gas control valve, lease water valve, test fluid inlet valve, and selector valve and opening the by-pass valve, permitting the oil, water, and gas if present to settle and stratify;

g. then closing the purge valve opening the gas vent valve, and opening the lease water valve, injecting lease water into the chamber to pass gas through said gas flow meter;

h. then opening the gas vent valve and lease water valve, and closing the test fluid inlet valve and purge valve, and purging gas from the vessel until a gas/oil interface is sensed by the sensor;

i. then closing the gas vent valve and opening the selector valve, forcing oil from the chamber until an oil/water interface is sensed by the probe, then also opening said gas vent valve and continuing the supply of lease water for a period of time to flush the gas line and return line beyond the flow meter, and measuring the volume of oil by calculating the time of flow before the oil/water interface was sensed.

11. A process according to claim 10 in which gas is controllably by-passed around said gas vent valve to said gas flow meter when the volummetric relationship of gas to oil is excessive to such extent as to frustrate the collection of an oil sample of suitable volume.

* * * * *